United States Patent [19]

Leveque et al.

[11] 4,392,498
[45] Jul. 12, 1983

[54] APPARATUS INTENDED FOR CLASSIFYING THE QUANTITY OF A FATTY PRODUCT FOUND ON THE SKIN SURFACE

[75] Inventors: Jean-Luc M. Leveque, Montfermeil; Gilbert J. Gras, Aulnay-sous-Bois, both of France

[73] Assignee: L'Oreal, Paris, France

[21] Appl. No.: 252,489

[22] Filed: Apr. 8, 1981

[30] Foreign Application Priority Data

Apr. 9, 1980 [FR] France ................................ 80 07961

[51] Int. Cl.³ ............................................... A61B 5/00
[52] U.S. Cl. ..................................... 128/665; 128/664
[58] Field of Search ............... 128/665, 666, 667, 632, 128/734; 340/753, 754, 870.38; 356/41, 229, 445, 443; 250/214 R, 565

[56] References Cited

U.S. PATENT DOCUMENTS

| 3,927,317 | 12/1975 | Liedholz | 250/565 |
| 3,927,571 | 12/1975 | Athey | 340/870.38 |
| 3,995,959 | 12/1976 | Shaber | 356/443 |
| 4,027,981 | 6/1977 | Steinbatz | 356/229 |
| 4,333,016 | 6/1982 | Bilstad et al. | 250/214 R |

FOREIGN PATENT DOCUMENTS

2022818 12/1979 United Kingdom ............... 318/675

Primary Examiner—Richard J. Apley
Assistant Examiner—George Yanulis
Attorney, Agent, or Firm—N. Jerome Rudy

[57] ABSTRACT

Measurements of the greasiness of skin are made by applying a plate against a region of skin to be studied and then inserting the plate in a recess of the casing, in register with a photodiode and a phototransistor. A series of n (in this case 5) indicator lamps is connected to a set of $n-1$ (in this case 4) comparators each comparing a respective voltage threshold level with the voltage delivered by the photoresistor, so that the voltage of the transistor, and hence the greasiness of the deposit on the plate through which luminous flux from the photodiode to the phototransistor passes by reflection from the upper side of the plate, can be determined by observing which lamps are illuminated.

14 Claims, 5 Drawing Figures

APPARATUS INTENDED FOR CLASSIFYING THE QUANTITY OF A FATTY PRODUCT FOUND ON THE SKIN SURFACE

DESCRIPTION

The present invention relates to an apparatus to be used for determining the quantity of a fatty or greasy product, for instance of sebum, found on the skin surface of a living subject. This determination is effected by means of signal lamps which light up selectively according to the quantity of sebum found in one or other of a multiplicity of predetermined classes.

In U.S. patent application Ser. No. 844,038 (now abandoned to the benefit of the two Continuation-In-Part Applications Ser. No. 27,718 and Ser. No. 27,717) there has already been described an apparatus to be used for determining the quantity of sebum secreted by a skin, on the basis of measuring an optical characteristic of a specimen. In the said U.S. patent application Ser. No. 844,038 a luminous flux modulated at a fixed frequency is directed on to a plate having a ground surface, which plate has previously been applied in a predetermined way to a region of skin to be examined, and the flux emanating from the plate is measured by a flux receiver which only takes account of luminous flux having the particular frequency modulation of the transmitter. From this received flux "data" it is possible to deduce the data elements for determining the sebum secretion of the skin region against which the ground-surfaced plate has been applied. In a variant of this apparatus, the ground glass plate comprises a reflecting rear side, so luminous emission of a photodiode is directed onto the said plate and is reflected towards a phototransistor whose output provides a measurement of the quantity of sebum secreted by the skin. The measurement thus obtained is independent of the external light conditions by reason of the modulation of the luminous flux. This device gives every satisfaction, but has the drawback of being relatively expensive taking into account the electronic circuit which is necessarily associated with the emitter photodiode and the receiver phototransistor.

In British Patent Application No. 2022818A there has also been proposed a simple design of apparatus for determining the sebum quantity secreted by a skin region. In this apparatus, the casing contains inside a light emitter supplying a continuous luminous flux towards a sight which carries at least one mark or scale capable of being positioned within the casing opposite the translucent element on which the sebum of the skin region to be examined has been deposited. The evaluation of the sebum quantity is effected by observing the aforementioned mark through the abovementioned translucent element. This device is fairly cheap but gives results which essentially depend on the visual evaluation made by the user.

The object of the present invention is to provide apparatus to be used for determining the quantity of fatty products carried by a skin, the said apparatus being capable of inexpensive manufacture but nevertheless making it possible to dispense with any need for visual evaluation by the user. Thus the apparatus according to the invention has the advantage that it can be used by any user, even an unskilled user, to give uniform results in all cases, this advantage being obtained whilst maintaining a moderate cost. The apparatus according to the invention may in particular be used for (a) determining the quantity of sebum secreted by the skin or for (b) determining the quantity of oil remaining, after a certain time, on a skin which after the application of the said oil has absorbed a proportion thereof.

Accordingly the present invention provides apparatus to be used for the classification of the skin of a living subject into n predetermined classes where n is an integer greater than one, the said classification being effected according to the quantity of product carried by the said skin, such apparatus comprising: a translucent element having two surfaces of which one surface is to be applied in a predetermined way on skin to be examined; a luminous flux emitter arranged to irradiate said translucent element; a luminous flux receiver positioned to receive luminous flux from said irradiated translucent element; and means for comparing the output of the flux receiver with (n−1) predetermined threshold values to produce a display of at least one of n possible luminous indications representing the abovementioned n classes.

The apparatus according to the invention allows the skin examined to be classified in a certain number of predetermined categories, this classification being automatically effected by the lighting up of light signals, each one of which corresponds to a predetermined skin category.

In a preferred embodiment, the flux emitter may be designed to emit a continuous flux; the translucent element may be a ground-surfaced plate of which the side which does not receive the luminous flux constitutes a plane mirror; the ground-surfaced plate may, in particular, be made of glass, of a plastic material, or of sapphire; the flux emitter may be a photodiode; the flux receiver may be a phototransistor; the output voltage supplied by the phototransistor receiver may be forwarded in parallel to (n−1) comparators, each one of which receives on its other input a respective one of several predetermined threshold voltages; the ground plate constituting the translucent element may be arranged opposite the flux emitter and receiver and be held longitudinally in guides of a casing of the apparatus and cooperate, by that one of its edges which are perpendicular to the guides which is first introduced into the said guides, with a switch controlling the electric supply of the flux emitter.

In a first variant of the apparatus according to the invention, the outputs of the (n−1) comparators are interconnected in parallel on the same line and are separated from each other by at least one photodiode, each one of the n skin classes being associated with a respective photodiode constituting a signal lamp; the line interconnecting the output of the comparators may be connected by its two end terminals to the opposite polarities of the electricity supply, at least one photodiode being provided between each terminal and the adjacent comparator; a safety diode may be placed in series with the photodiode constituting the signal lamp between the terminal connected to the positive lead and the output of the adjacent comparator.

In a second variant of the embodiment of the apparatus according to the invention, each one of the (n−1) comparators is connected to a decoder assembly whose output feeds a display unit capable of displaying a number taken from a set of n numbers, each one of which numbers is assigned to a respective one of the predetermined n skin classes; the decoder assembly may be constituted by a multiplicity of logic gates and may forward a binary code signal to the display unit.

In a third variant of the embodiment of the apparatus according to the invention, the output of the receiver phototransistor is connected to the frame by a parallel pair comprising on the one hand a resistor at the terminal at which the voltage which is applied to the $(n-1)$ comparators is taken, and on the other hand a capacitor; in this way, the voltage supplied by the photoreceiver to the comparator inputs is established with a progressiveness according to the capacitance of the capacitor and the changeover of the outputs of those of the comparators which have to change in view of the final value attained by the output voltage of the photoreceiver, is effected with a time shift; the outputs of the $(n-1)$ comparators are connected in parallel to the input of the read-out device, the said read-out device comprising a pulse counter capable of supplying a numerical display according to the number of pulses received; the output of each one of the comparators is provided with a circuit transforming a change in voltage level into a pulse and with an insulating diode.

It has been found that the apparatus according to the invention has made it possible to effect the classification of an examined skin region very satisfactorily into a number of predetermined classes. In fact, it is known that there exists a good correlation between the transparence of, on the other hand, a ground strip applied beforehand for some time and with a given pressure to the skin region to be examined, and on the other hand the quantity of the fatty products deposited on the said strip. In dependence on the transparence of the ground strip subjected to examination in the apparatus according to the invention, one or other of the signal lamps of the apparatus lights up which determines the class of the examined skin without the need for assessment by the user of the apparatus. Moreover, the emission of the photodiode used as the flux emitter is not subject to ageing, and the response of the apparatus is therefore constant in respect to time.

To render the invention more readily understood an embodiment of the apparatus of the invention will now be described by way of a purely illustrative and non-restrictive example, shown with reference to the accompanying drawings, in which.

Figure 1:
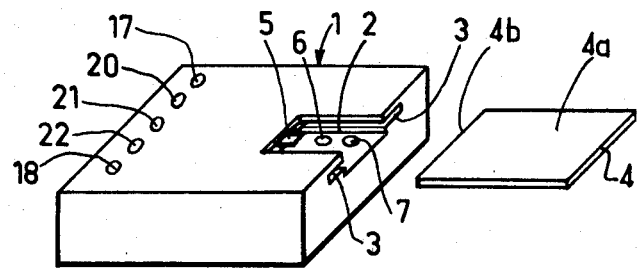
FIG. 1 shows in perspective an external view of the casing of the apparatus according to the invention.

Referring to the drawing, it will be seen that the casing of the apparatus according to the invention as a whole has been designated as 1. Casing 1 has a parallelpiped shape and has on one of its edges a recess 2 having a substantially rectangular plan view. Recess 2 comprises on its two longitudinal edges guides 3 which slidably receive the longitudinal edges of a plate 4 having a ground surface, in this case a ground glass plate. Plate 4 comprises a metallised side 4a which constitutes a plane mirror and it is intended to slide in the guides 3 so as to be received in the recess 2. When plate 4 is thus positioned in the casing 1, its front transverse edge 4b cooperates with the moving contact of a switch 5 so that, when the plate 4 is pushed home in the recess 2, switch 5 is closed whereas on the contrary when this pressure is not effected the switch 5 remains in an open position.

The apparatus described is intended to be used for classifying the various skin regions presented to the user of the apparatus into appropriate ones of five categories, from the point of view of their sebum secretion. This classification is based on the fact that a strip of ground glass, such as strip 4, has a degree of transparence varying according to the quantity of sebum which is disposed on its non-metallised side. The user thus needs to apply such a plate 4 during a given time and with a given pressure against the skin region to be examined and it is known that in this case, the quantity of sebum deposited on plate 4 is the greater, the greater the secretion of the skin region being investigated. In other words, the greater the secretion of sebum of the skin region examined, the more transparent the plate 4 becomes. Hence, all that is necessary is to determine the transparence of plate 4 in order to define the "greasiness" class of the skin region being examined.

The principle of the apparatus according to the invention lies in directing a monochromatic luminous flux from a photodiode 6 on to the ground side of plate 4 and recovering this luminous flux after passage one way through the thickness of plate 4, then reflection at the metallised surface 4a and finally, a return passage through the thickness of plate 4 on to the base of a phototransistor 7 which has an output voltage substantially proportional to the luminous flux received. The distances on the one hand between photodiode 6 and the plate 4, and on the other hand between the plate 4 and the phototransistor 7 are clearly determined since precise positioning of plate 4 within housing 2 is ensured by means of guides 3 and since the photodiode 6 and photoresistor 7 are arranged at the bottom of recess 2. In these circumstances, there exists a relation between the quantity q of the sebum deposited on plate 4 (expressed in $\mu g/cm^2$) and the voltage V expressed in mV at the output of phototransistor 7. The curve representing the variation of V as a function of q is given in FIG. 2; of course, this curve presupposes a given level for the luminous emission of photodiode 6.

Using the apparatus described, the various skin regions which may be submitted for examination are to be classified into five distinct categories. To do this, four category limits are defined, corresponding to four values of the quantity of sebum deposited on plate 4 during one application operation on the skin according to the adopted procedure (using a constant predetermined time of application and pressure of application).

Figure 2:
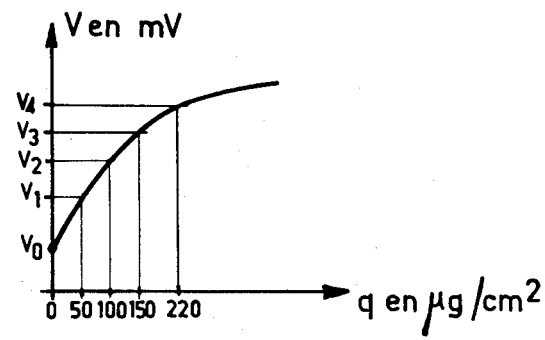
FIG. 2 is a graph giving the relationship between quantity q of the sebum deposited on the ground-surfaced plate and the voltage V obtained at the output of the flux receiver of the apparatus according to the invention.

The abovementioned four limits have been represented in FIG. 2 as corresponding respectively to 50, 100, 150 and 220 microgrammes of sebum per $cm^2$ of the plate 4. Each one of these limits corresponds to the output voltages $V_1$, $V_2$, $V_3$, $V_4$ of the phototransistor 7. The first skin category is that in respect of which the sebum deposit is below 50 microgrammes per $cm^2$; for this category, the output voltage of the phototransistor is between $V_0$ and $V_1$; for the second category, the sebum quantity is between 50 and 100 microgrammes per cm² and the output voltage of the phototransistor 7 is between $V_1$ and $V_2$; for the third category, the sebum quantity is between 100 and 150 microgrammes per cm² and the voltage between $V_2$ and $V_3$; for the fourth category, the sebum quantity is comprised between 150 and 220 microgrammes per cm² and the voltage is between $V_3$ and $V_4$; and for the fifth category, the sebum quantity exceeds 220 microgrammes per cm² and the voltage is higher than $V_4$.

Figure 3:
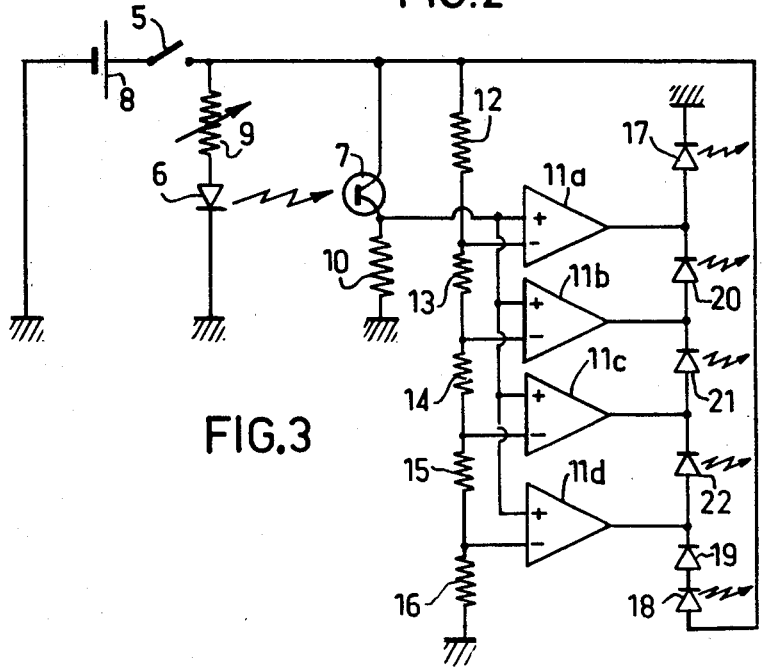
FIG. 3 represents the electronic circuit diagram of a first variant of the electronic circuit of the apparatus according to the invention.

The electronic circuit of a first variant of the apparatus according to the invention is schematically represented in FIG. 3. It will be seen that this circuit is energised by a battery 8 giving a 9 volt voltage supply. Switch 5 is in series with battery 8 to control supply to the emitter photodiode 6 via an adjustable resistor 9. Phototransistor 7 receives on its base the luminous emission transmitted by the plate 4. The voltage of the battery 8 is applied to the emitter of phototransistor 7 and the collector is connected to the frame via a resistor 10. The output voltage V of the phototransistor 7 is the voltage at the terminals of resistor 10 which thus serves to adjust the sensitivity of the apparatus.

The output voltage of phototransistor 7 is applied to the positive inputs of four comparators 11a, 11b, 11c and 11d. The negative inputs of these same four comparators are connected to the electric supply and to the frame via resistors 12, 13, 14, 15 and 16 which together define a multi-step potential divider. The resistor 12 is interposed between the positive lead and the negative terminal of comparator 11a; the resistor 13 is interposed between the negative terminals of the comparators 11a and 11b; the resistor 14 is interposed between the negative terminals of the comparators 11b and 11c; the resistor 15 is interposed between the negative terminals of the comparators 11c and 11d; and the resistor 16 is interposed between the negative terminal of comparator 11d and the frame. The outputs of the four comparators 11a, 11b, 11c and 11d are connected in parallel on a line which is established between the positive lead and the frame and comprises a given number of diodes. A first photodiode 17 is connected between comparator 11a and the frame; photodiode 18 and a safety diode 19 are connected between the comparator 11d and the positive lead, (the safety diode 19 being disposed between the output of comparator 11d and the photodiode 18); and photodiodes 20, 21 and 22, respectively, are interposed between the comparators 11a–11b, 11b–11c, and 11c–11d. The photodiodes 18, 22, 21, 20 and 17 of this set constitute the five signal lamps of the apparatus and are intended to indicate to the user that the skin region examined corresponds to the particular one of the five predetermined classes pertinent to the signal lamp which illuminates. The abovementioned five signal lamps therefore appear along one of the edges of casing 1 of the apparatus; the corresponding photodiodes have a current limiting resistor incorporated to conserve the energy of battery 8.

The functioning of the device which has been described above is easy to explain: the user, having applied plate 4 against the skin region to be examined, arranges this plate in the recess 2 of the apparatus and pushes the plate 4 to the end of the recess to actuate switch 5 (FIGS. 1 and 3). When switch 5 is closed, photodiode 6 emits a continuous luminous flux which passes through the plate 4, is reflected on metallised surface 4a, returns through the plate 4 and is received on the base of phototransistor 7. The voltage thus obtained at the output of the phototransistor 7 is applied to the positive inputs of the four comparators 11a, 11b, 11c and 11d.

If there is a low output voltage, that is to say a small quantity of sebum has been deposited on plate 4, the voltage on the positive input of comparator 11d is below the reference voltage on its negative input (determined by the values of the resistors 12, 13, 14, 15, 16). In that case, the output of comparator 11d is at zero and photodiode 18 lights up whereas the photodiodes 17, 20, 21 and 22 remain extinguished. If the quantity of sebum on plate 4 is increased sufficiently, the output voltage of the phototransistor 7 is increased and attains the higher reference voltage obtained on the negative terminal of comparator 11d. At this instant, the comparator 11d changes over and supplies a voltage of $(9-\epsilon)$ volts on its output, where $\epsilon$ corresponds to the drop in the internal voltage of the comparator. Photodiode 18 is extinguished while, on the other hand, photodiode 22 lights up; however, the other photodiodes remain extinguished. To allow for the case where $\epsilon$ may have a value higher than the voltage drop in the photodiodes used, there has been added in series with photodiode 18, a safety diode 19 which makes it possible to ensure the definite extinction of photodiode 18 at the time when comparator 11d changes over.

If the quantity of sebum on plate 4 is increased still further, the output voltage of phototransistor 7 increases to attain a value equal to the voltage applied to the negative terminal of comparator 11c. In this case, comparator 11c changes over, causing photodiode 22 to be extinguished and photodiode 21 to be illuminated. In this case, there is no risk of photodiode 22 remaining illuminated because the comparators 11c and 11d are identical and therefore have the same internal voltage drop. It will therefore be seen that as the quantity of sebum on plate 4 increases, lighting up of firstly the photodiode 21, then photodiode 20 and finally photodiode 17, for the highest quantity of sebum occurs. No two photodiodes remain illuminated simultaneously. Thus a single photodiode is illuminated to correspond to a skin category defined by the limits 0, 50, 100, 150, 220 microgrammes per cm² specifically set out in FIG. 2.

It should be noted that the presence of the adjustable resistor 9 allows for any production tolerances of the photodiode 6 and the phototransistor 7 to be compensated, so the apparatus according to the invention may be accurately adjusted in spite of the production tolerances obtaining in the case of the electronic components used.

Figure 4:
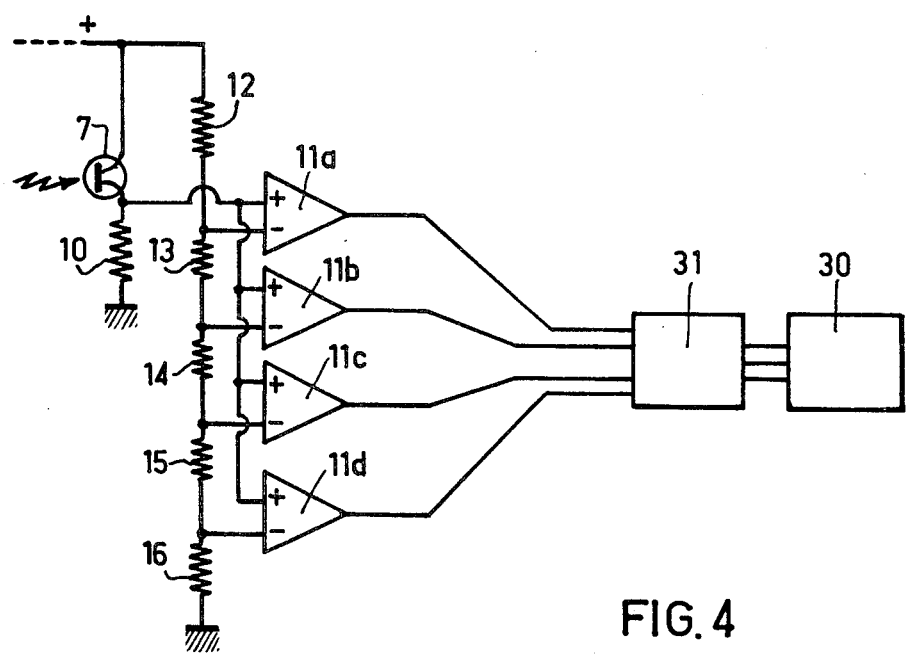
FIG. 4 represents that part of the circuit which is downstream of the photoreceiver, for a second variant of the electronic circuit of the apparatus according to the invention.

FIG. 4 partly represents the electronic circuit corresponding to a second variant of the embodiment of the apparatus according to the invention. FIG. 4 only shows the part of the circuit which is downstream of the photoreceiver 7, the part that is upstream being strictly identical to that represented in FIG. 3. In the circuit of FIG. 4, the elements which are identical with those described in the first variant, for example the photoreceiver 7 and its associated resistor 10, have been designated by the same reference numbers. The voltage at the terminal connecting the photoreceiver 7 to the resistor 10 is applied to the positive inputs of comparators 11a, 11b, 11c and 11d. The negative inputs of these comparators are supplied with reference voltage values defined by resistors 12, 13, 14, 15 and 16. The whole part of this circuit is identical with the corresponding one in the first variant.

In this second variant, however, the outputs of the four comparators are applied to a decoder unit 31. It is clear that each comparator output is, according to the output voltage of photoreceiver 7, either at zero level or at level 1, so that for each measurement effected by the apparatus according to the invention the decoder unit 31 is receiving a code corresponding to that indicated in the table below. In this Table, S denotes the output voltage at the terminals of the resistor 10, and S1, S2, S3 and S4 respectively denote the threshold voltage values relating to the comparators 11d, 11c, 11b and 11a and defined by the set of the resistors 12, 13, 14, 15 and 16. When voltage S is below the value of S1, the outputs of all the comparators are at zero; when voltage S reaches the value S1, the comparator 11d changes over and delivers at its output a voltage equal to the supply voltage less the internal voltage drop of the comparator 11d, this value being considered as corresponding to level 1. The Table below gives in its second column the output states of the four comparators depending on the value of voltage S in relation to the four thresholds S1, S2, S3, S4 (indicated in the first column).

| Value of S | Output levels of the comparators 11d 11c 11b 11a | Sebum deposits on plate | Binary code supplied by decoder 31 | Display on Device 30 |
|---|---|---|---|---|
| S ≦ S1 | 0 0 0 0 | from 0 to 50 μg/cm² | 000 | 0 |
| S1 < S ≦ S2 | 1 0 0 0 | from 50 to 100 μg/cm² | 001 | 1 |
| S2 < S ≦ S3 | 1 1 0 0 | from 100 to 150 μg/cm² | 010 | 2 |
| S3 < S ≦ S4 | 1 1 1 0 | from 150 to 220 μg/cm² | 011 | 3 |
| S4 < S | 1 1 1 1 | exceeding 220 μg/cm² | 100 | 4 |

The four threshold values S1, S2, S3, S4 define five possible states corresponding to the quantities of sebum applied to the ground-surfaced plate 4 of the apparatus; these stages being the same as those defined for the first variant of the embodiment previously described. The quantities of sebum corresponding to these five classes are indicated in the third column of the above Table. The decoder unit 31 is constituted by an assembly of logic gates which, on receipt of the codes indicated in the second column of the Table above, supplies at its output the binary codes indicated in the fourth column of the Table above. These three figure binary codes are directed to a read-out device 30 which displays the decimal number corresponding to the binary code received. The decimal number in question is indicated in the fifth column of the Table above. It will thus be seen that this second variant makes it possible to display, on a screen, the number of the skin class corresponding to the deposit of sebum effected on the ground-surfaced plate by the skin region under examination by the apparatus according to the invention. This mode of display may, in certain cases, be preferable to the lighting up of one of a series of photodiodes.

Figure 5:
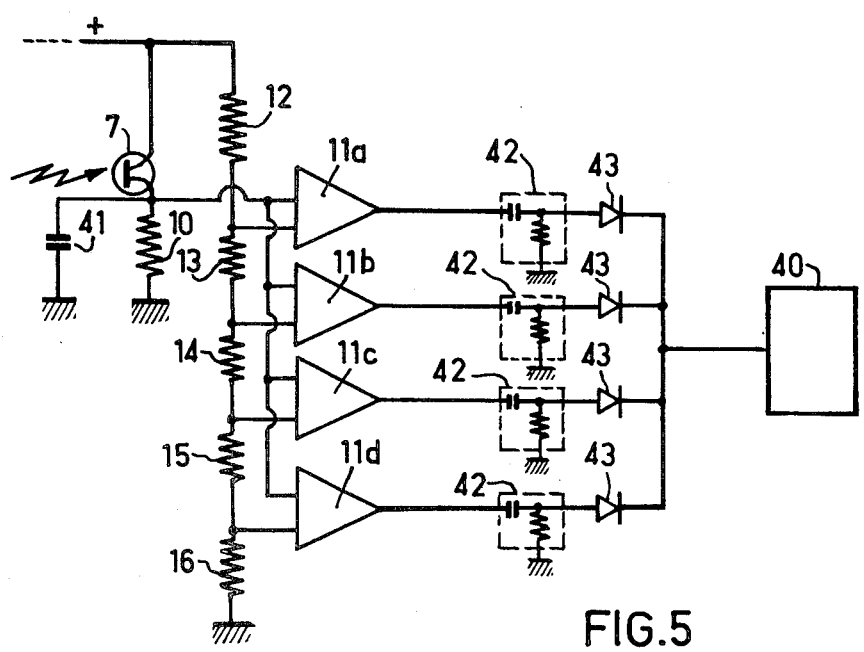
FIG. 5 represents the part of the circuit which is downstream of the photoreceiver for a third variant of the electronic circuit of the apparatus according to the invention.

In FIG. 5, there is represented a third variant of the electronic circuit of the apparatus according to the invention; this representation has been effected as a partial representation and (like FIG. 4) relates only to the components downstream of photoreceiver 7; the circuit upstream of the said photoreceiver being strictly identical with that which has been described in detail with regard to the first variant and shown in FIG. 3. In this third variant, several components are strictly identical with those used in the first variant and these components (such as photoreceiver 7 with its emitter connected to the frame via a resistor 10 and having the voltage at a point between the photoreceiver and the resistor applied to the positive terminals of four comparators 11a, 11b, 11c, 11d) have been designated by the same reference numbers as in the first variant. As in FIG. 3, the negative terminals of the four comparators receive the voltage threshold values defined by the resistors 12, 13, 14, 15 and 16.

In the first variant, when the ground-surfaced plate 4 is placed in position in the apparatus, the photoreceiver 7 receives on its base a quantity of light and delivers at its emitter a voltage which is instantaneously established at the value corresponding to the quantity of sebum carried by the ground-surfaced plate 4 under examination.

In the third variant, shown in FIG. 5, an attempt has been made to spread out in time the voltage rise of the emitter of the photoreceiver; to do this, provision has been made for a 10 micro-farad capacitor 41 to be connected in parallel with the resistor 10. In this way, the rise in voltage at the positive terminals of the four comparators 11a, 11b, 11c, 11d is effected gradually from zero up to the maximum value S corresponding to the quantity of sebum deposited on the plate 4 under examination. According to the position of value S in relation to the four threshold voltage values S1, S2, S3 and S4 relating to the four comparators 11d, 11c, 11b and 11a, as the voltage on the emitter of photoreceiver 7 is being established, none of the comparator outputs will change over if value S is below all the threshold values, or the four outputs of the four comparators will successively change over if value S is higher than all the threshold values, or a certain number of the comparators will successively change over if value S is an intermediate value between the two abovementioned extreme cases.

At the output of each of the comparators, there has been arranged a respective circuit 42 supplying a pulse at its output at the instant when its input is subjected to the rising front corresponding to the change-over of the associated comparator. Such a circuit 42 is of a known form, constituted by a capacitor whose output is connected to the frame via a resistor. The output of each of the four circuits 42 is provided with an insulating diode 43 and is fed to the single input of a pulse counter 40. It is clear that, according to the value of voltage S, the pulse counter 40 will receive a different number of pulses corresponding to the number of comparators whose outputs have changed over. Spreading out the voltage rise of the emitter of photoreceiver 7 makes it possible to separate in time the pulses corresponding to the change-over of the comparators. The pulse counter 40 makes it possible to display, on a screen, a numerical indication corresponding to the number of pulses received. Such a counter is well known in the art and is, for instance, marketed under reference "TIL 306" by the "TEXAS INSTRUMENTS" Company. It will thus be seen that this third variant again provides for a numerical display corresponding to the number allotted to the skin category whose sebum secretion is subjected to examination.

It is clear that the apparatus which has been described may be extremely moderately priced and may be made very compact in size. Moreover, the determination effected by this apparatus is totally independent of the user's faculties of observation.

We claim:

1. Apparatus for the classification of the skin of a living subject into n predetermined classes where n is an integer greater than one, the said classification being effected according to the quantity of fatty product carried by the said skin, such apparatus comprising:
  (a) a translucent element having two surfaces of which one surface is to be applied under predetermined conditions on skin to be examined;
  (b) frame means to hold said translucent element in a predetermined position;
  (c) a luminous flux emitter arranged to irradiate said translucent element in said predetermined position;
  (d) a luminous flux receiver positioned to receive luminous flux from said irradiated translucent element in said predetermined position;
  (e) means for supplying (n−1) predetermined threshold voltage values;
  (f) means for comparing the output of the flux receiver with said (n−1) predetermined voltage values; and
  (g) display means responsive to said comparing means to produce display of at least one of n possible luminous indications representing the said n classes.

2. Apparatus according to claim 1, wherein the translucent element is a plate having a ground said surface, and a said surface which constitutes a plane mirror.

3. Apparatus according to claim 1 or 2, wherein said flux emitter is constructed to emit a continuous luminous flux.

4. Apparatus according to claim 1, wherein said flux emitter is a photodiode.

5. Apparatus according to any one of claims 1 to 4, wherein said flux receiver is a phototransistor.

6. Apparatus according to claim 5, wherein said comparing means comprise (n−1) comparators having outputs and further having first and second inputs, including means for applying the output voltage of said phototransistor in parallel to said first inputs of said (n−1) comparators, and means associated with said threshold voltage value supplying means for applying each of said predetermined voltage threshold values to said second input of a respective one of said (n−1) comparators.

7. Apparatus according to claim 6, including a line which includes at least n photodiodes serving as said display means; means connecting said outputs of said (n−1) comparators in parallel, with their outputs connected to said line at points which are separated from each other by at least a respective one said photodiode, each one of the n skin classes being associated with one said photodiode.

8. Apparatus according to claim 7, wherein said line connecting the outputs of the comparators has two end terminals and including means connecting said end terminals to the respective positive and negative electricity supply leads, there being at least one respective said photodiode between each said end terminal and the adjacent comparator.

9. Apparatus according to claim 8, and including one further diode in series with that of said respective photodiodes which constitutes the said luminous indication between that said end terminal connected to the positive supply lead and the output of the said adjacent comparator thereto.

10. Apparatus according to claim 6, including a read-out device effective to display a numeral taken from a set of n numerals, each one of which is assigned to a respective one of the n predetermined skin categories; decoder means feeding said read out device; and means connecting each of the (n−1) comparators to said decoder means.

11. Apparatus according to claim 10, wherein said decoder means comprises a multiplicity of logic gates and is effective to deliver a binary code to said read-out device.

12. Apparatus according to claim 6, wherein said phototransistor has an output, and including (i) means connecting said output to said frame means, said last means comprising a capacitor in parallel with a resistor, (ii) read-out means; (iii) means connecting a point between said phototransistor and said resistor to the inputs of the (n−1) comparators; and (iv) means connecting the outputs of said (n−1) comparators in parallel to the input of said read-out means, said read-out means including pulse counter means capable of energising a numerical display in response to the number of pulses received.

13. Apparatus according to claim 12, wherein the output of each of the comparators is provided with a respective circuit means effective to transform a change in voltage level at that output into a pulse and with an insulating diode.

14. Apparatus according to one of claims 1 to 13, wherein said translucent element is a plate having first and second opposed edges, and said frame means include longitudinal guide means holding said plate in said predetermined position in relation to the emitter and the flux receiver, and including a switch for controlling the electricity supply to the flux emitter, said guide means being effective to receive said plate slidably with said first and second edges transverse to the direction of sliding and said switch being positioned to cooperate with one of the edges of the plate which is first introduced into the said guides.

* * * * *